(12) United States Patent
Palin et al.

(10) Patent No.: US 11,094,418 B2
(45) Date of Patent: Aug. 17, 2021

(54) OPTIMIZED BIOLOGICAL MEASUREMENT

(71) Applicant: Nokia Technologies Oy, Espoo (FI)

(72) Inventors: Arto Tapio Palin, Viiala (FI); Teemu Ilmari Savolainen, Nokia (FI); Jukka Pekka Reunamäki, Tampere (FI)

(73) Assignee: Nokia Technologies Oy, Espoo (FI)

( * ) Notice: Subject to any disclaimer, the term of this patent is extended or adjusted under 35 U.S.C. 154(b) by 693 days.

(21) Appl. No.: 14/985,480

(22) Filed: Dec. 31, 2015

(65) Prior Publication Data

US 2017/0188969 A1   Jul. 6, 2017

(51) Int. Cl.
| | | |
|---|---|---|
| *G16H 50/30* | (2018.01) | |
| *A61B 5/00* | (2006.01) | |
| *A61B 5/024* | (2006.01) | |
| *A61B 5/0245* | (2006.01) | |
| *A61B 5/117* | (2016.01) | |
| *A61B 5/145* | (2006.01) | |
| *A61B 5/1455* | (2006.01) | |
| *G06F 19/00* | (2018.01) | |
| *A61B 5/369* | (2021.01) | |

(52) U.S. Cl.
CPC .......... *G16H 50/30* (2018.01); *A61B 5/0002* (2013.01); *A61B 5/0245* (2013.01); *A61B 5/02405* (2013.01); *A61B 5/02416* (2013.01); *A61B 5/117* (2013.01); *A61B 5/14532* (2013.01); *A61B 5/14551* (2013.01); *A61B 5/369* (2021.01); *A61B 5/7275* (2013.01); *G06F 19/00* (2013.01); *A61B 5/0077* (2013.01)

(58) Field of Classification Search
CPC ................................. G06Q 50/22–24
See application file for complete search history.

(56) References Cited

U.S. PATENT DOCUMENTS

| | | | |
|---|---|---|---|
| 7,765,039 B1* | 7/2010 | Hagenbuch | G07C 5/085 701/32.2 |
| 8,475,367 B1* | 7/2013 | Yuen | A61B 5/02007 600/300 |
| 2005/0065569 A1* | 3/2005 | Ricci | A61N 1/37254 607/32 |
| 2005/0119532 A1* | 6/2005 | Cloutier | A61B 5/0002 600/300 |
| 2009/0082823 A1* | 3/2009 | Shuros | A61N 1/36535 607/17 |
| 2009/0326353 A1* | 12/2009 | Watson | A61B 5/6814 600/330 |
| 2010/0127705 A1* | 5/2010 | Scharfetter | A61B 5/05 324/310 |
| 2012/0059267 A1* | 3/2012 | Lamego | A61B 5/022 600/483 |
| 2012/0157263 A1* | 6/2012 | Sivak | G06F 3/014 482/4 |

(Continued)

*Primary Examiner* — Robert A Sorey
(74) *Attorney, Agent, or Firm* — Laine IP Oy (57) ABSTRACT

According to an example aspect of the present invention, there is provided an apparatus comprising a memory configured to store sensor data obtained from a person, and at least one processing core configured to perform a determination, based at least partly on the stored sensor data, concerning whether conditions are propitious to a biological measurement, and responsive to the conditions being determined to be propitious, to cause a triggering signal to be initiated concerning the biological measurement.

18 Claims, 5 Drawing Sheets

(56) References Cited

U.S. PATENT DOCUMENTS

| | | | | |
|---|---|---|---|---|
| 2013/0085348 A1* | 4/2013 | Devenyi | A61B 5/1118 |
| | | | 600/301 |
| 2013/0326600 A1* | 12/2013 | Sorek | G06Q 20/4016 |
| | | | 726/6 |
| 2014/0108029 A1* | 4/2014 | Kim | G16H 80/00 |
| | | | 705/2 |
| 2014/0155705 A1* | 6/2014 | Papadopoulos | A61B 5/0004 |
| | | | 600/301 |
| 2015/0015400 A1* | 1/2015 | Davis | G08B 21/06 |
| | | | 340/575 |
| 2015/0084859 A1* | 3/2015 | Itzhaik | G06K 9/00355 |
| | | | 345/156 |
| 2015/0272454 A1* | 10/2015 | Damiano | G16H 10/60 |
| | | | 600/490 |
| 2016/0066847 A1* | 3/2016 | Sales | A61B 5/1114 |
| | | | 600/324 |
| 2017/0026238 A1* | 1/2017 | Pignataro | G01R 21/133 |
| 2017/0358182 A1* | 12/2017 | El-Iraki | G08B 29/185 |
| 2018/0143150 A1* | 5/2018 | Bezemer | A61B 5/721 |
| 2018/0280624 A1* | 10/2018 | Bitton | A61M 5/31525 |

\* cited by examiner

OPTIMIZED BIOLOGICAL MEASUREMENT

FIELD

The present invention relates to managing biological measurements.

BACKGROUND

Healthcare solutions continue to develop. Reasons behind this trend include that more and more health conditions can be detected and improved, that people live longer than before, and that people have more resources to be used for healthcare. However, at the same time, health care units and hospitals are working at their limits and countries are increasingly struggling to maintain the level of resourcing currently provided for healthcare.

In order to sustain the current overall level of healthcare, to improve efficiency, to reduce waste, and to make proper healthcare available to more people, the healthcare cycle, including hospital days, should be optimized to save money and, more importantly, to release capacity for new patients. Additionally, patients are often willing to leave hospital as soon as possible to return home, and to reduce a risk of contracting an infection due to prolonged time in hospital.

One solution to reduce the number of days spent in hospital is to move the patient to home care as soon as possible. Earlier this has not been possible, but nowadays technology allows creation of devices that may be used to remotely monitor patients' status at home environments. This makes it possible to organize good home care systems and thus improve overall healthcare systems and procedures.

Monitoring patient status may comprise performing a measurement of a biological parameter, such as, for example, a blood pressure measurement. Monitoring may comprise, where applicable, a video monitoring arrangement, a voice connection to a dispatcher station and/or visits by nurses to provide company and advice relating to medications, nutrition and physical exercise, for example.

SUMMARY OF THE INVENTION

The invention is defined by the features of the independent claims. Some specific embodiments are defined in the dependent claims.

According to a first aspect of the present invention, there is provided an apparatus comprising a memory configured to store sensor data obtained from a person, and at least one processing core configured to perform a determination, based at least partly on the stored sensor data, concerning whether conditions are propitious to a biological measurement, and responsive to the conditions being determined to be propitious, to cause a triggering signal to be initiated concerning the biological measurement.

Various embodiments of the first aspect may comprise at least one feature from the following bulleted list:
- the sensor data comprises historical sensor data obtained in the past
- the sensor data comprises at least one of: recent movement data, posture data, recent pulse rate, recent heart rate variability, electrocardiograph data and plethysmograph data
- the determination is further based at least partly on at least one of the following: a time of day, a time since a most recent previous biological measurement and a measurement configuration
- the sensor data comprises reference data characterising the person, and the determination comprises a determination as to whether recently obtained sensor data matches the reference data
- the determination comprises determining that plural sensors, from each of which the apparatus is arranged to receive a concurrent sensor data feed, are measuring the same person
- the apparatus is configured to provide the triggering signal to a biological sensor, to thereby cause the biological measurement to take place as a response to the triggering signal
- the apparatus is configured to provide the triggering signal to a user interface device, to thereby cause the user interface device to advise a user to perform the biological measurement
- the at least one processing core is configured to perform a second determination, after the biological measurement, based at least partly on sensor data obtained during the biological measurement, concerning whether the biological measurement is to be at least one of: accepted, discarded, provided with metadata indicating unreliability or provided with an indication of the sensor data obtained during the biological measurement
- the second determination is based on at least one of the following: determining whether the person moved during the biological measurement, determining whether an elevation used in the biological measurement was correct.

According to a second aspect of the present invention, there is provided a method comprising storing sensor data obtained from a person, performing a determination, based at least partly on the stored sensor data, concerning whether conditions are propitious to a biological measurement, and causing a triggering signal to be initiated concerning the biological measurement responsive to the conditions being determined to be propitious.

Various embodiments of the second aspect may comprise at least one feature from the following bulleted list:
- the sensor data comprises historical sensor data obtained in the past
- the sensor data comprises at least one of: recent movement data, posture data, recent pulse rate, recent heart rate variability, electrocardiograph data and plethysmograph data
- the determination is further based at least partly on at least one of the following: a time of day, a time since a most recent previous biological measurement and a measurement configuration
- the sensor data comprises reference data characterising the person, and the determination comprises a determination as to whether recently obtained sensor data matches the reference data
- the determination comprises determining that plural sensors, from each of which the apparatus is arranged to receive a concurrent sensor data feed, are measuring the same person
- the apparatus is configured to provide the triggering signal to a biological sensor, to thereby cause the biological measurement to take place as a response to the triggering signal
- the apparatus is configured to provide the triggering signal to a user interface device, to thereby cause the user interface device to advise a user to perform the biological measurement the at least one processing core is configured to perform a second determination, after the biological measurement, based at least partly on sensor data obtained during the biological measurement, concerning whether the biological measurement is to be at least one of: accepted, discarded, provided with metadata indicating unreliability or provided with an indication of the sensor data obtained during the blood pressure measurement the second determination is based on at least one of the following: determining whether the person moved during the biological measurement, determining whether an elevation used in the biological measurement was correct.

According to a third aspect of the present invention, there is provided an apparatus comprising means for storing sensor data obtained from a person, means for performing a determination, based at least partly on the stored sensor data, concerning whether conditions are propitious to a biological measurement, and means for causing a triggering signal to be initiated concerning the biological measurement responsive to the conditions being determined to be propitious.

According to a fourth aspect of the present invention, there is provided a non-transitory computer readable medium having stored thereon a set of computer readable instructions that, when executed by at least one processor, cause an apparatus to at least store sensor data obtained from a person, perform a determination, based at least partly on the stored sensor data, concerning whether conditions are propitious to a biological measurement, and cause a triggering signal to be initiated concerning the biological measurement responsive to the conditions being determined to be propitious.

According to a fifth aspect of the present invention, there is provided a computer program configured to cause a method in accordance with the second aspect to be performed

EMBODIMENTS

Sensor data may be used in determining a propitious time to perform a biological measurement on a person, such as a blood pressure measurement. The sensor data may indicate, for example, that the person is essentially at rest, is the correct person, is in approximately a correct physical posture and/or has not moved energetically in the recent past. The time of day may also be looked at, for example to increase a suitability of measurements for the purpose of comparing them to earlier and future measurements of the same person.

Figure 1:
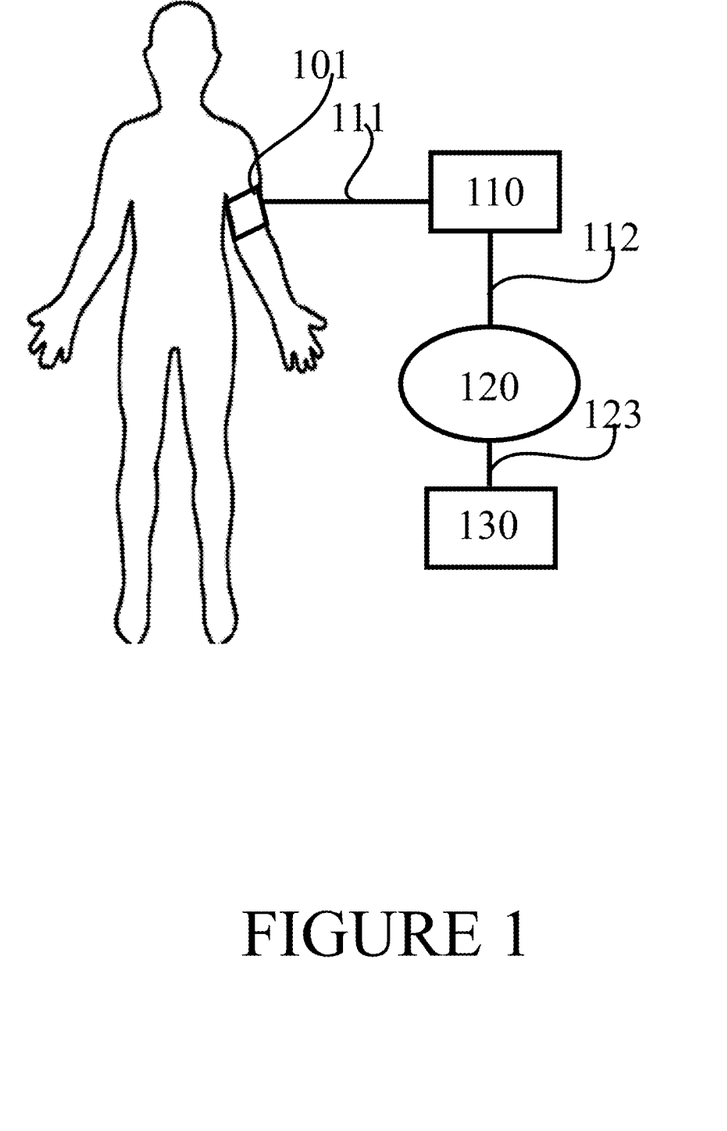
FIG. 1 illustrates an example system in accordance with at least some embodiments of the present invention.

FIG. 1 illustrates an example system in accordance with at least some embodiments of the present invention. The system comprises a biosensor 101, which may comprise, for example, a blood pressure measurement cuff and/or a photoplethysmograph sensor.

Conventional blood pressure measuring apparatuses which use pulse waves are roughly classified into the photoplethysmography type, pressure plethysmography type, and Korotkoff type, according to their measurement principles. With the photoplethysmography type, light reflected by blood flowing through a part squeezed by a cuff is obtained as a pulse wave signal by a photosensor. With the pressure plethysmography type, the oscillation of blood vessel walls caused by blood flowing through a part squeezed by a cuff is obtained as a pulse wave signal by a pressure sensor. With the Korotkoff type, Korotkoff sounds produced due to squeezing by a cuff are obtained as a pulse wave signal by a microphone installed near the cuff. Blood pressure is measured as the variation of the obtained pulse wave signal with time.

Monitoring patient status may comprise performing a measurement of a biological parameter, such as, for example, a blood pressure measurement, a blood oxygen level measurement, a blood sugar measurement or an electrical measurement of brain activity. A further example is electrocardiography, ECG. In general, biosensor 101 may comprise a sensor or sensor arrangement suitable for obtaining data for a biological measurement. Where biosensor 101 is arranged to measure electrical brain activity, it may be attachable, at least party, on the head rather than the arm, as illustrated in FIG. 1. In general, a measurement of a biological parameter may be referred to as a biological measurement. For example, the biological parameter may be a vital parameter and/or a parameter of a human person. A biological measurement may be non-therapeutic in the sense that it does not constitute therapy but the obtaining of information from the person. While biosensor 101 is illustrated as a single sensor apparatus in FIG. 1, in some embodiments biosensor 101 comprises a set of sensor apparatuses, the set comprising more than one sensor apparatus.

Biosensor 101 is communicatively coupled, via interface 111, to gateway 110. Gateway 110 may be a wearable device, in which case it is attachable to the body of the person. Alternatively, gateway 110 may be a distinct, non-wearable device. Gateway 110 may be configured to receive information from biosensor 101, such as, for example, sensor data that biosensor 101 has obtained by performing a biological measurement. The sensor data may be related to blood pressure, blood oxygen level, blood sugar level or electric brain activity, for example. Gateway 110 may instruct biosensor 101 to perform a biological measurement, such instructing comprising signalling via interface 111. Sensor data relating to electric brain activity may comprise electroencephalographic data, for example. Biosensor 101 may, alternatively to being distinct from gateway 110, be comprised in gateway 110.

Gateway 110 may be in communication with a server 130 via network 120. Network 120 may comprise one or more networks, which may comprise the Internet, for example. Interface 112 connects gateway 110 to network 120, and interface 123 connects server 130 to network 120. Server 130 may comprise a cloud server, and/or a secure healthcare service server, for example.

Interface 111 may comprise a wire-line or wireless connection. For example, it may comprise a Bluetooth™, WLAN, NFC, USB, WCDMA or LTE or other suitable connection. Interface 112 may comprise a wire-line or wireless connection. For example, interface 112 may comprise a WLAN, Ethernet, WCDMA, LTE or DSL connection, at least in part. Interface 123 may comprise an Ethernet or DSL connection, for example. A protocol connection between gateway 110 and server 130 may be encrypted end-to-end, for example using public key cryptography, a symmetric encryption algorithm or a one-time pad, for example. Interface 111 may be encrypted, to thereby protect personal information from being unintentionally disclosed.

A biological measurement, such as for example a blood pressure measurement, involves measuring a dynamic variable. As such, the sensor data produced by such a measurement may be a result of an interplay between an underlying value and a time-varying fluctuation. For example, a person may have a base blood pressure, which may be momentarily increased as a response to physical exertion, or momentarily reduced as a response to a relaxation exercise. The base blood pressure is here the underlying value, and the responses to physical exertion and relaxation are a time-varying fluctuation.

To facilitate comparison of biological measurements to each other, for example to determine whether a person's blood pressure is trending higher or lower in the long term, it should be attempted to measure the underlying value. In other words, the measurement should be performed at a time, when the time-varying fluctuation has little impact on the result.

Gateway 110 or server 130 may be configured to determine, whether conditions are propitious to a biological measurement, such as a blood pressure measurement, for example. By propitious it is meant that the conditions are such that the time-varying fluctuation is not so large as to meaningfully affect the measurement. In other words, while the conditions need not be absolutely optimal, they are good enough to produce a measurement that may be used comparatively, that is, compared to past and/or future measurements of a same type.

The determination concerning whether the conditions are propitious may be based, at least partly, on sensor data. The sensor data may be collected in the past, for example including in the recent past, for example over a past 30 seconds. For example, the determination may comprise determining a heart rate is stable and/or not excessively high or low, indicating the person is in a neutral level of physical exertion. A non-stable heart rate, that is a heart rate that exhibits variability, may be an indication of stress, which may affect a biological measurement, such as blood pressure. Alternatively or additionally, the sensor data may comprise motion sensor data, such as acceleration sensor data, whereby it may be determined, if the person is moving. In case the person is moving, the conditions may be considered as not propitious. Heart rate data may be obtained via an electrocardiograph sensor or from photoplethysmograph data, for example.

The determination may be based, at least partly, on movement and/or posture data, such that the conditions are considered propitious when the person is in a similar state of movement and/or posture as during previous measurements of the same type. For example, a sitting posture and still movement state may be considered propitious for a blood pressure measurement.

The determination may further be based on a time of day, such that biological measurements are preferably performed at the same, or comparable, times of day. Some biological indicators exhibit circadian variation, wherefore to produce results that are well comparable to each other, it is most useful to perform measurements at roughly the same time of day. Additionally or alternatively, the determination may be based on a length of time that has elapsed since a previous measurement. To track a long-term trend, it may be more useful to measure once a week for a year, than to perform 52 measurements during a single day, for example. Therefore, from this aspect, a time condition may be propitious where more than a minimum, but less than a maximum, length of time has elapsed from the previous measurement. The previous measurement in this context comprises the most recent previous measurement, in other words the immediately preceding previous measurement in a sequence. As a specific example, a time condition may be seen as propitious at measurement rate windows, wherein a window exists once a day or once a week. In case one window is missed, the time condition will, in this example, be propitious again during the next window. A measurement configuration may further affect the determination. A measurement configuration may comprise information relating to a time of day, week or month the measurement is to be performed. A measurement configuration may comprise information relating to an alert or problem identified in a previous measurement.

The determination may be based on reference data characterizing the person, to help ensure the measurement is going to be conducted on the correct person. Again, measuring the correct person and not another person can facilitate comparing measurements with each other. The reference data may comprise sensor data obtained from the person under medical supervision. The reference data may comprise heart rate characteristics, for example. The reference data may comprise a fingerprint, In addition or alternatively, the reference data may comprise acceleration data characterizing the movement and posture of the person. Using the reference data, it may be prevented that an elderly person requests a younger relative to provide a good measurement, for example to conceal a medical condition from medical staff. Exchange of encryption keys for use between gateway 110 and server 130 may be performed at the same time as obtaining reference data, in case the reference data is obtained in a controlled environment.

A controlled blood pressure measurement using a cuff may be performed to calibrate a pulse transmit time, PTT, measured with plethysmograph and electrocardiography, ECG used to enable continuous blood pressure measurements. The controlled measurement may involve wireless synchronization of the blood pressure and ECG measurements, for example.

In case more than one sensor is used, the determination as to whether the conditions are propitious to a biological measurement may comprise a determination concerning whether the more than one sensor are attached to the same person. This, in turn, may comprise a determination concerning whether sensor data from the sensors is consistent with each other. For example, if the sensors report pulses that are not synchronized, it may be the sensors are measuring pulses of two different persons. Likewise, in case blood oxygen levels are different between sensors, the sensors may be attached to two different persons with distinct blood oxygen levels. To enable this, sensors may be furnished with capability to cross-check their readings, such that the sensors may in part duplicate each other's capabilities. Such a determination may take place in gateway 110 or in server 130, based on sensor data received in server 130 from gateway 110, for example.

Responsive to the conditions being determined to be propitious, gateway 110 or server 130 may initiate a triggering signal concerning the biological measurement. The triggering signal may be provided, via interface 111, to biosensor 101 to thereby cause biosensor 101 to perform the measurement. Biosensor 101 may, for example, have continuous access to the biological variable to be measured, wherein causing the measurement to occur may simply comprise causing biosensor 101 to record a result from the continuously available variable. Alternatively, biosensor 101 may be triggered to initiate a measurement sequence to obtain the measurement result. As a yet further alternative, the triggering signal may be provided to a user interface element, such as a display and/or a loudspeaker, to provide an instruction to the person or another user to perform the measurement.

During the measurement, gateway 110 or server 130 may monitor the conditions, and after the measurement is completed it may be determined, in a second determination, whether the conditions were propitious for the duration of the measurement. The second determination may be based on sensor data obtained, for example from biosensor 101 and/or from other sensors, during the biological measurement or when the measurements are being analysed afterwards by the gateway 110 or by the server 130. In case a disturbance is detected during the measurement, the measurement result may be discarded or provided with metadata indicating unreliability. In case no disturbance is detected, the measurement result may be accepted, wherein being accepted may comprise being transmitted to server 130, for example. As an example, in case the user moves energetically during a blood pressure measurement, the measurement may be affected by a time-varying fluctuation caused by the movement, rendering the result less suitable for comparing with other measurement results from the same person.

As an option, after the second determination the measurement result may be provided with metadata that characterizes the sensor data obtained during the biological measurement, this sensor data being other than the measurement result itself. Such metadata may enable using the measurement result in a way that takes the disturbance into account, for example where the sensor data indicates movement during the biological measurement, a correcting factor may be applied to attenuate the effect of the associated time-varying fluctuation.

An elevation of biosensor 101 may be employed in the first and/or the second determination. The elevation, by which it is meant a relative height, may be determined using radio techniques or, where applicable, barometry. Employing elevation, it may be controlled that the person is in a sitting posture, for example, when the biological measurements are carried out.

Figure 2:
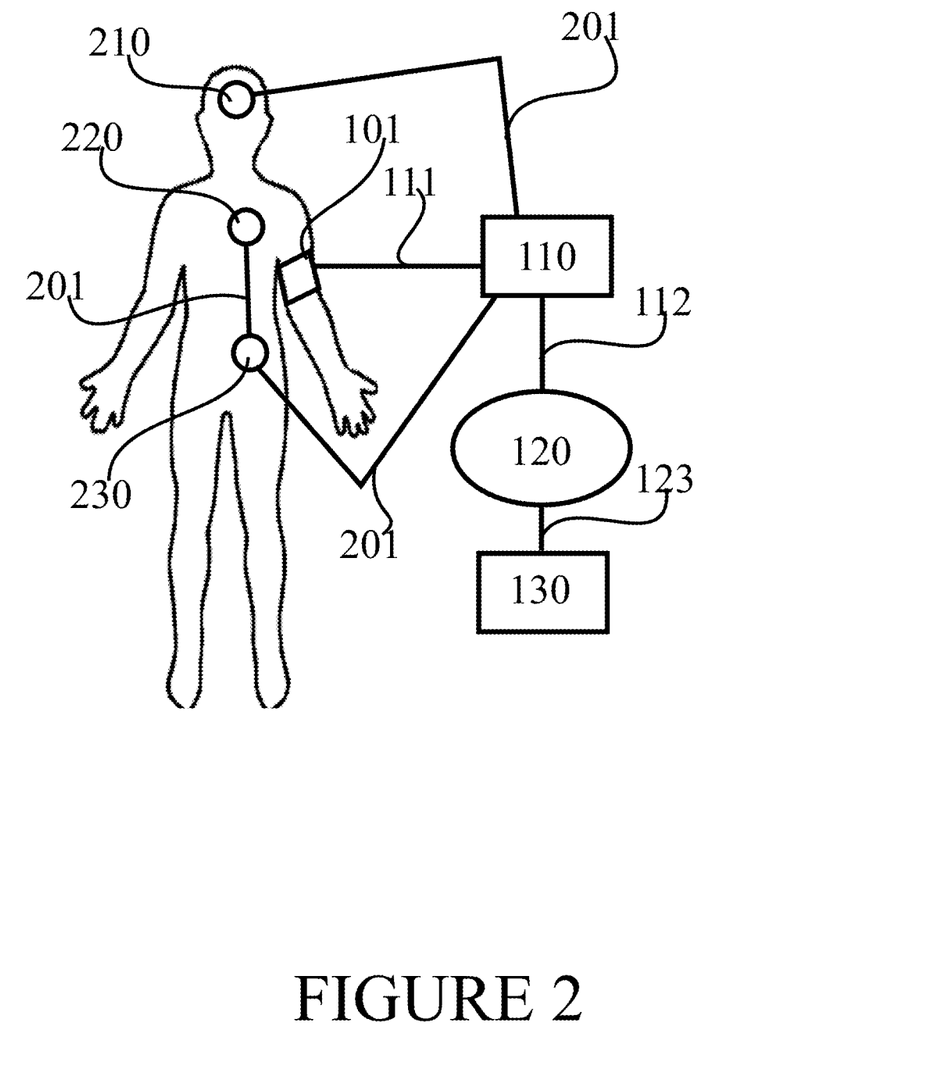
FIG. 2 illustrates an example system in accordance with at least some embodiments of the present invention.

FIG. 2 illustrates an example system in accordance with at least some embodiments of the present invention. Like numbering denotes like structure as in FIG. 1.

In addition to elements illustrated in FIG. 1, the system of FIG. 2 illustrates sensors 210, 220 and 230, as well as sensor interfaces 201 configured to couple sensors 210, 220 and 230 with gateway 110. Sensor interfaces 201 may comprise any suitable network of connections enabled to convey sensor data from sensors 210, 220 and 230 to gateway 110. For example, sensor interfaces 201 may comprise wire-line or low-power wireless connections.

A plurality of sensors comprising sensors 210, 220, 230 and biosensor 101 may together be used to determine whether conditions are propitious to the biological measurement. Data from a plurality of sensors, which may comprise sensors of different types, may together be more capable of discriminating between propitious and non-propitious conditions. For example, at least one of sensors 210, 220 and 230 may comprise a brain electrical pulse sensor, a heart rate sensor, a blood sugar level sensor and a blood oxygen level sensor. At least one of the sensors may be arranged to determine a posture in which the person is. At least two of the sensors may be arranged to, together, determine, at least in part, a posture in which the person is.

Where it is determined, either in the FIG. 1 or the FIG. 2 case, that conditions are not propitious to the biological measurement, the person may be advised, for example automatically, concerning why the conditions are not propitious, to enable the person to correct the conditions. Thus, an indication may be provided to advise the person to sit down, lie down, or to simply wait a few moments without moving much, for example.

Either in the FIG. 1 or the FIG. 2 case, if biosensor 101 has continuous access to the biological variable to be measured, gateway 110 or server 130 may collect measurement results from biosensor 101 based on determinations the conditions are propitious for such a measurement. In this case, the person may wear the sensor or sensors, and the person need not even be informed when a measurement is performed. In this way, gateway 110 or server 130 may collect a series of biological measurements automatically, during normal life of the person. In this case, gateway 110 or server 130 may monitor the conditions continuously, or, for example, around the times when a measurement is desired, and collect the measurement result when conditions are propitious.

Figure 3:
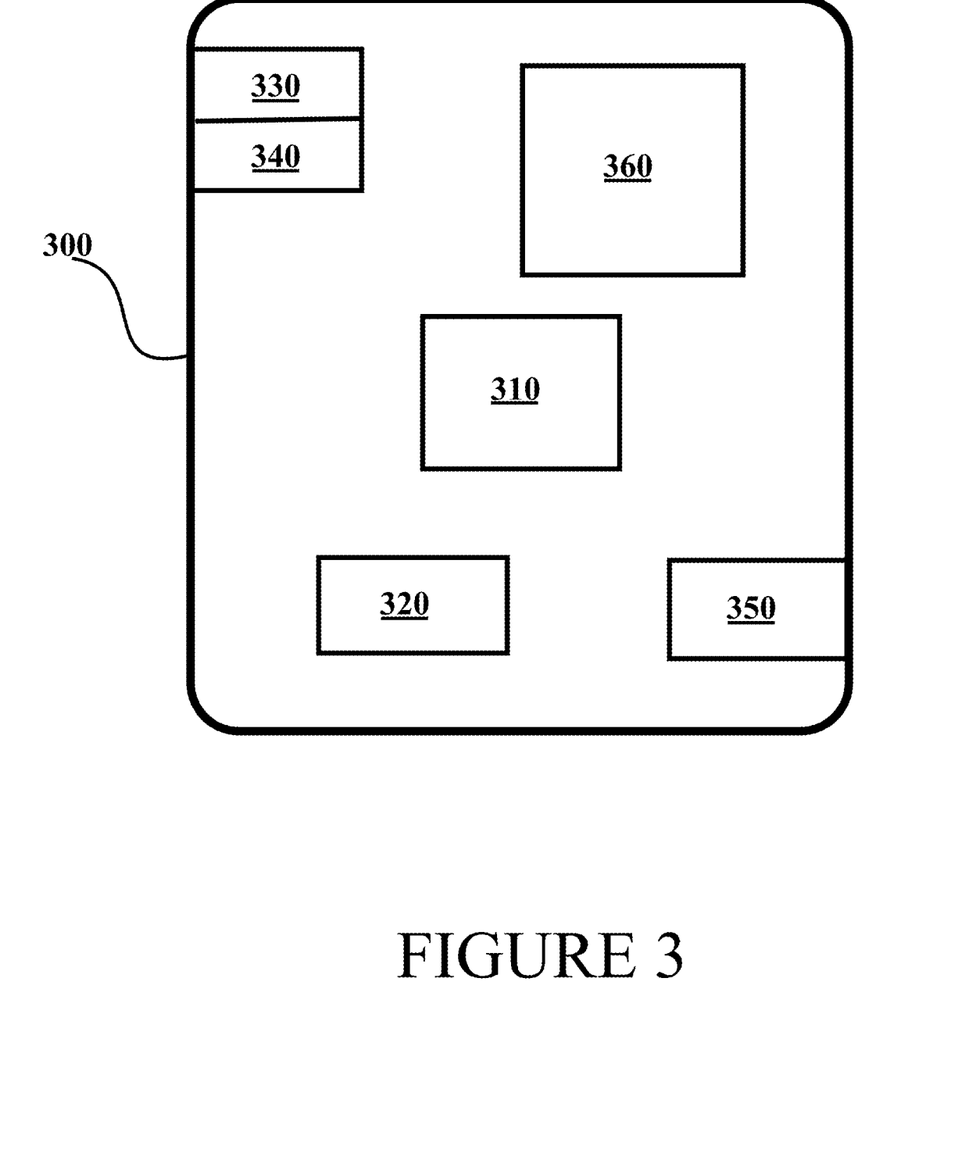
FIG. 3 illustrates an example apparatus capable of supporting at least some embodiments of the present invention.

FIG. 3 illustrates an example apparatus capable of supporting at least some embodiments of the present invention. Illustrated is device 300, which may comprise, for example, a gateway 110 or server 130 of FIG. 1 or FIG. 2. Comprised in device 300 is processor 310, which may comprise, for example, a single- or multi-core processor wherein a single-core processor comprises one processing core and a multi-core processor comprises more than one processing core. Processor 310 may comprise more than one processor. A processing core may comprise, for example, a Cortex-A8 processing core manufactured by ARM Holdings or a Steamroller processing core produced by Advanced Micro Devices Corporation. Processor 310 may comprise at least one Qualcomm Snapdragon and/or Intel Atom processor. Processor 310 may comprise at least one application-specific integrated circuit, ASIC. Processor 310 may comprise at least one field-programmable gate array, FPGA. Processor 310 may be means for performing method steps in device 300. Processor 310 may be configured, at least in part by computer instructions, to perform actions.

Device 300 may comprise memory 320. Memory 320 may comprise random-access memory and/or permanent memory. Memory 320 may comprise at least one RAM chip. Memory 320 may comprise solid-state, magnetic, optical and/or holographic memory, for example. Memory 320 may be at least in part accessible to processor 310. Memory 320 may be at least in part comprised in processor 310. Memory 320 may be means for storing information. Memory 320 may comprise computer instructions that processor 310 is configured to execute. When computer instructions configured to cause processor 310 to perform certain actions are stored in memory 320, and device 300 overall is configured to run under the direction of processor 310 using computer instructions from memory 320, processor 310 and/or its at least one processing core may be considered to be configured to perform said certain actions. Memory 320 may be at least in part comprised in processor 310. Memory 320 may be at least in part external to device 300 but accessible to device 300.

Device 300 may comprise a transmitter 330. Device 300 may comprise a receiver 340. Transmitter 330 and receiver 340 may be configured to transmit and receive, respectively, information in accordance with at least one cellular or non-cellular standard. Transmitter 330 may comprise more than one transmitter. Receiver 340 may comprise more than one receiver. Transmitter 330 and/or receiver 340 may be configured to operate in accordance with global system for mobile communication, GSM, wideband code division multiple access, WCDMA, long term evolution, LTE, IS-95, wireless local area network, WLAN, Ethernet and/or worldwide interoperability for microwave access, WiMAX, standards, for example.

Device 300 may comprise a near-field communication, NFC, transceiver 350. NFC transceiver 350 may support at least one NFC technology, such as NFC, Bluetooth, Bluetooth Low Energy (BLE) or similar technologies.

Device 300 may comprise user interface, UI, 360. UI 360 may comprise at least one of a display, a keyboard, a touchscreen, a vibrator arranged to signal to a user by causing device 300 to vibrate, a speaker and a microphone. A user may be able to operate device 300 via UI 360, for example to control biological measurements.

Processor 310 may be furnished with a transmitter arranged to output information from processor 310, via electrical leads internal to device 300, to other devices comprised in device 300. Such a transmitter may comprise a serial bus transmitter arranged to, for example, output information via at least one electrical lead to memory 320 for storage therein. Alternatively to a serial bus, the transmitter may comprise a parallel bus transmitter. Likewise processor 310 may comprise a receiver arranged to receive information in processor 310, via electrical leads internal to device 300, from other devices comprised in device 300. Such a receiver may comprise a serial bus receiver arranged to, for example, receive information via at least one electrical lead from receiver 340 for processing in processor 310. Alternatively to a serial bus, the receiver may comprise a parallel bus receiver.

Device 300 may comprise further devices not illustrated in FIG. 3. For example, where device 300 comprises a smartphone, it may comprise at least one digital camera. Some devices 300 may comprise a back-facing camera and a front-facing camera, wherein the back-facing camera may be intended for digital photography and the front-facing camera for video telephony. Device 300 may comprise a fingerprint sensor arranged to authenticate, at least in part, a user of device 300. In some embodiments, device 300 lacks at least one device described above.

Processor 310, memory 320, transmitter 330, receiver 340, NFC transceiver 350 and/or UI 360 may be interconnected by electrical leads internal to device 300 in a multitude of different ways. For example, each of the aforementioned devices may be separately connected to a master bus internal to device 300, to allow for the devices to exchange information. However, as the skilled person will appreciate, this is only one example and depending on the embodiment various ways of interconnecting at least two of the aforementioned devices may be selected without departing from the scope of the present invention.

Figure 4:
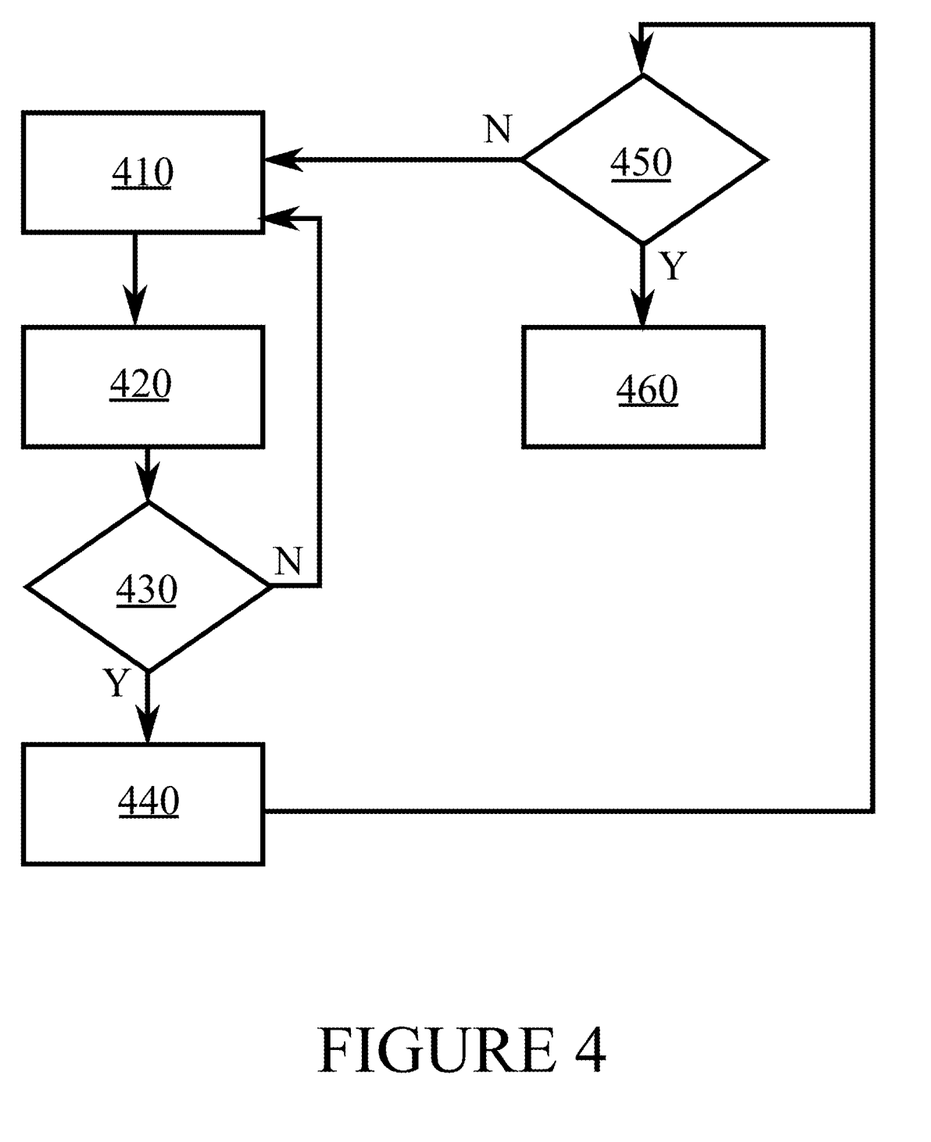
FIG. 4 is a flow graph of a method in accordance with at least some embodiments of the present invention.

FIG. 4 is a flow graph of a method in accordance with at least some embodiments of the present invention. Processing begins in phase 410, where sensor data is collected, for example using biosensor 101 and/or at least one of sensors 210, 220 and 230. In phase 420, the sensor data collected in phase 410 is stored, for example in gateway 110 and/or server 130.

In phase 430, a determination is performed concerning whether conditions are propitious to a biological measurement, such as, for example, a blood pressure or ECG measurement, as described above. In case the conditions are determined to be propitious, processing advances from phase 430 to phase 440. Else, processing advances from phase 430 back to phase 410.

In phase 440, the biological measurement is triggered and performed, such that a measurement result is thereby obtained. Processing advances from phase 440 to phase 450. In phase 450, a second determination is performed, to determine whether the measurement result obtained in phase 440 can be accepted. For example, the second determination may comprise determining whether conditions were propitious during the entire time period when the measurement was performed (in step 440). Additionally or alternatively, the second determination may comprise determining whether the measurement was performed on the correct person, as described above.

In case the second determination indicates the measurement result can be accepted, the measurement result is stored, phase 460. In case the second determination indicates the measurement result cannot be accepted, processing returns to phase 410.

Processing of the phases of FIG. 4 may be performed in gateway 110 or server 130, or a first part of the phases may be performed in gateway 110 and a second part in server 130. For example, phases 410 and 420 may be performed in gateway 110 and phases 430, 450 and 460 in server 130.

Figure 5:
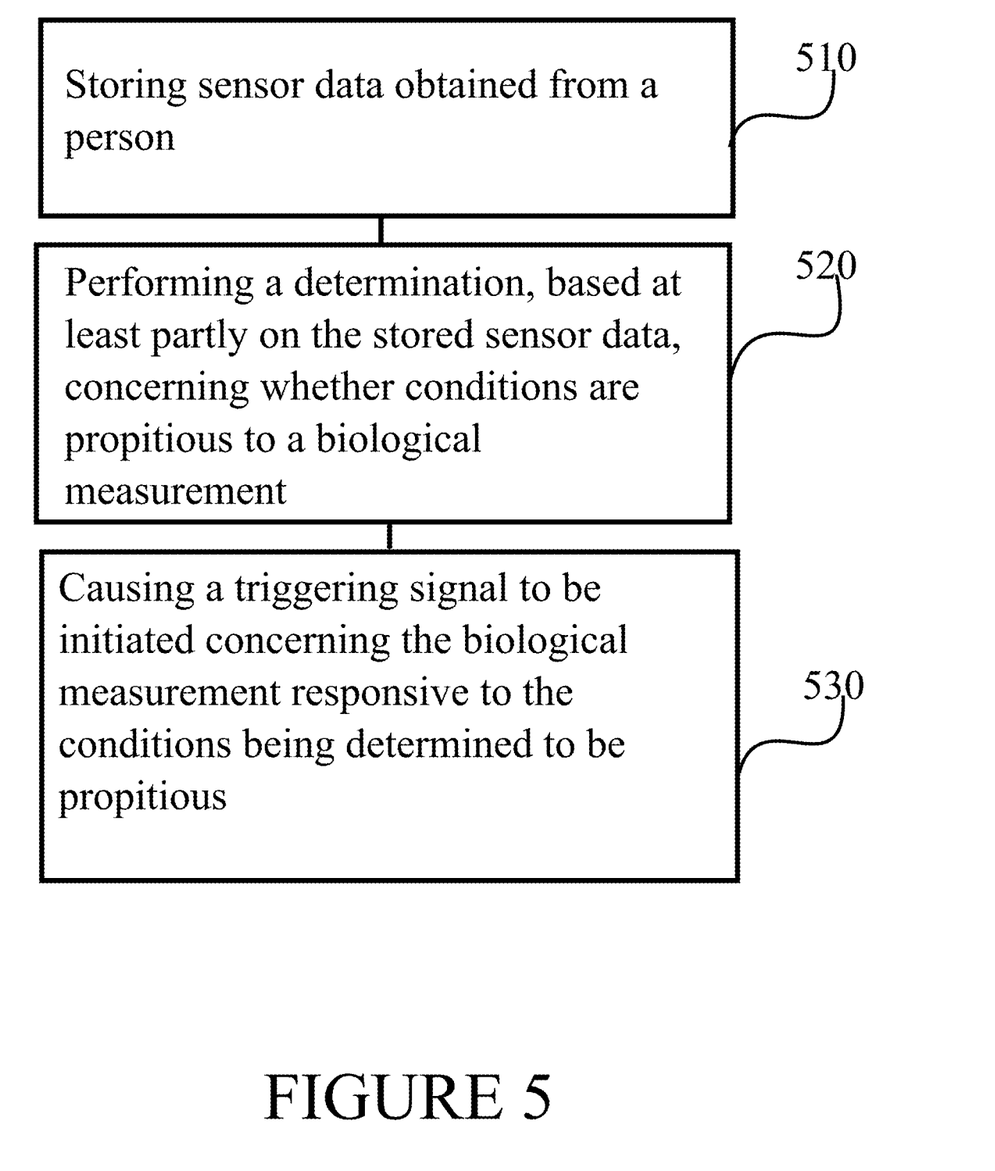
FIG. 5 is a flow graph of a method in accordance with at least some embodiments of the present invention.

FIG. 5 is a flow graph of a method in accordance with at least some embodiments of the present invention. The phases of the illustrated method may be performed in gateway 110 or server 130, for example.

Phase 510 comprises storing sensor data obtained from a person. Phase 520 comprises performing a determination, based at least partly on the stored sensor data, concerning whether conditions are propitious to a biological measurement. Finally, phase 530 comprises causing a triggering signal to be initiated concerning the biological measurement responsive to the conditions being determined to be propitious. The biological measurement may comprise at least one of the following: a blood pressure measurement, a blood sugar measurement, a blood oxygen measurement and a brain electrical measurement.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the preceding description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality. Patent rights to the invention claimed here in are sought, copyright to the figures is not sought.

INDUSTRIAL APPLICABILITY

At least some embodiments of the present invention find industrial application in increasing accuracy of blood pressure measurements.

ACRONYMS LIST

DSL Digital subscriber line
ECG Electrocardiography
LTE Long term evolution
NFC Near-field communication
USB Universal serial bus
WCDMA Wideband code division multiple access
WLAN Wireless local area network

| REFERENCE SIGNS LIST | |
| --- | --- |
| 101 | Biosensor |
| 111, 112, 123 | Interfaces |
| 110 | Gateway |
| 120 | Network |
| 130 | Server |
| 210, 220, 230 | Sensors |
| 310-360 | Structure of FIG. 3 |
| 410-450 | Phases of the method of FIG. 4 |
| 510-530 | Phases of the method of FIG. 5 |

The invention claimed is:

1. An apparatus comprising:
a biosensor,
a memory configured to store sensor data obtained from a person by at least one first sensor distinct from the biosensor, the sensor data characterising a state of movement and posture of the person, and
at least one processing core configured to perform a determination, based at least partly on the stored sensor data, concerning whether conditions are propitious to a biological measurement, and responsive to the conditions being determined to be propitious, to automatically cause a triggering signal to be provided to the biosensor distinct from the at least one first sensor, to thereby perform the biological measurement on the person by the biosensor to generate a measurement result, wherein the at least one processing core is configured, at least in part, to determine the conditions are propitious when the person is in a similar state of movement and posture as during previous biological measurements of a same type and wherein the at least one processing core is configured, at least in part, to determine the conditions are propitious by using reference data characterizing the person, the reference data comprising acceleration data characterizing movement and posture of the person.

2. The apparatus according to claim 1, wherein the sensor data comprises historical sensor data obtained in the past.

3. The apparatus according to claim 1, wherein the sensor data comprises at least one of: recent pulse rate, recent heart rate variability, electrocardiograph data and plethysmograph data.

4. The apparatus according to claim 1, wherein the determination is further based at least partly on at least one of the following: a time of day, a time since a most recent previous biological measurement and a measurement configuration.

5. The apparatus according to claim 1, wherein the sensor data comprises the reference data characterising the person, and the determination comprises a determination as to whether recently obtained sensor data matches the reference data.

6. The apparatus according to claim 1, wherein the determination comprises determining that plural sensors, from each of which the apparatus is arranged to receive a concurrent sensor data feed, are measuring the same person.

7. The apparatus according to claim 1, wherein the at least one processing core is configured to perform a second determination, after the biological measurement, based at least partly on sensor data obtained during the biological measurement, concerning whether the biological measurement is to be at least one of: accepted, discarded, provided with metadata indicating unreliability or provided with an indication of the sensor data obtained during the biological measurement.

8. The apparatus according to claim 7, wherein the second determination is based on at least one of the following: determining whether the person moved during the biological measurement, determining whether an elevation used in the biological measurement was correct.

9. The apparatus according to claim 1, wherein the biological measurement comprises a blood pressure measurement.

10. A method in an apparatus comprising:
storing sensor data obtained from a person by at least one first sensor distinct from a biosensor comprised in the apparatus, the sensor data characterising a state of movement and posture of the person;

performing a determination, based at least partly on the stored sensor data, concerning whether conditions are propitious to a biological measurement, and causing, automatically and responsive to the conditions being determined to be propitious, a triggering signal to be provided to a biosensor distinct from the at least one first sensor, to thereby perform the biological measurement on the person by the biosensor to generate a measurement result, wherein the conditions are at least in part determined to be propitious when the person is in a similar state of movement and posture as during previous biological measurements of a same type, and wherein the determining the conditions are propitious comprises using reference data characterizing the person, the reference data comprising acceleration data characterizing movement and posture of the person.

11. The method according to claim 10, wherein the sensor data comprises historical sensor data obtained in the past.

12. The method according to claim 10, wherein the sensor data comprises at least one of: recent pulse rate, recent heart rate variability, electrocardiograph data and plethysmograph data.

13. The method according to claim 10, wherein the determination is further based at least partly on at least one of the following: a time of day, a time since a most recent previous biological measurement and a measurement configuration.

14. The method according to claim 10, wherein the sensor data comprises the reference data characterising the person, and the determination comprises a determination as to whether recently obtained sensor data matches the reference data.

15. The method according to claim 10, wherein the determination comprises determining that plural sensors, from each of which the apparatus is arranged to receive a concurrent sensor data feed, are measuring the same person.

16. The method according to claim 10, wherein the at least one processing core is configured to perform a second determination, after the biological measurement, based at least partly on sensor data obtained during the biological measurement, concerning whether the biological measurement is to be at least one of: accepted, discarded, provided with metadata indicating unreliability or provided with an indication of the sensor data obtained during the biological measurement.

17. The method according to claim 16, wherein the second determination is based on at least one of the following: determining whether the person moved during the biological measurement, determining whether an elevation used in the biological measurement was correct.

18. A non-transitory computer readable medium having stored thereon a set of computer readable instructions that, when executed by at least one processor, cause an apparatus to at least:

store sensor data obtained from a person by at least one first sensor distinct from a biosensor comprised in the apparatus, the sensor data characterising a state of movement and posture of the person;

perform a determination, based at least partly on the stored sensor data, concerning whether conditions are propitious to a biological measurement, and cause, automatically and responsive to the conditions being determined to be propitious, a triggering signal to be provided to a biosensor distinct from the at least one first sensor, to thereby perform the biological measurement on the person by the biosensor to generate a measurement result, wherein the conditions are at least in part determined to be propitious when the person is in a similar state of movement and posture as during previous biological measurements of a same type, and wherein the determining the conditions are propitious comprises using reference data characterizing the person, the reference data comprising acceleration data characterizing movement and posture of the person.

* * * * *